United States Patent
Uchida et al.

(10) Patent No.: US 6,500,472 B2
(45) Date of Patent: Dec. 31, 2002

(54) FOLIC ACID AND/OR VITAMIN B12-LACTOFERRIN COMPLEX

(75) Inventors: Toshiaki Uchida, Kawagoe (JP); Toshiaki Suguri, Tokyo (JP); Singh Harjinder, Massey University (NZ)

(73) Assignee: Snow Brand Milk Products Co., Ltd., Hokkai-do (JP)

( * ) Notice: Subject to any disclaimer, the term of this patent is extended or adjusted under 35 U.S.C. 154(b) by 100 days.

(21) Appl. No.: 09/794,176

(22) Filed: Feb. 27, 2001

(65) Prior Publication Data

US 2001/0036500 A1 Nov. 1, 2001

(30) Foreign Application Priority Data

Feb. 28, 2000 (JP) ........................................ 2000-051807

(51) Int. Cl.[7] .............................................. A23L 1/302
(52) U.S. Cl. ......................... 426/72; 426/74; 530/400; 424/439; 514/904; 514/905
(58) Field of Search .............................. 426/72–74, 590; 424/439; 530/400; 514/904, 905

(56) References Cited

U.S. PATENT DOCUMENTS 5,008,120 A * 4/1991 Tanaka et al.
5,098,722 A * 3/1992 Tanaka et al.
5,116,953 A * 5/1992 Dosako et al.
5,340,924 A * 8/1994 Tomita et al.
6,258,383 B1 * 7/2002 Gohlke et al.

FOREIGN PATENT DOCUMENTS

JP 9107917 4/1997

OTHER PUBLICATIONS

Jacob, E. et al. 1974. Evidence against transferrin as a binder of either vitamin B12 or folic. Blood 43(5), 767.*

Peter W. Parodi, A role for milk proteins in cancer prevention, The Australian Journal of Dairy Technology vol. 53—Apr. 1998,pp37–47.

D. Tomeė, et al, Nutrional and Physiological Role of Milk Protein Components, Bull. I>D>F., vol. 336, 1998, pp. 11–16.

* cited by examiner

Primary Examiner—Carolyn Paden
(74) Attorney, Agent, or Firm—Knobbe, Martens Olson & Bear LLP

(57) ABSTRACT

Folic acid and/or vitamin $B_{12}$ and lactoferrin are mixed to produce a folic acid and/or vitamin $B_{12}$-lactoferrin complex. The complex can be used for enriching foods or drink.

15 Claims, No Drawings

FOLIC ACID AND/OR VITAMIN B12-LACTOFERRIN COMPLEX

BACKGROUND OF THE INVENTION

1. Field of the Invention

The present invention relates to a complex in which lactoferrin holds folic acid and/or vitamin $B_{12}$ (hereinafter referred to as folic acid and/or vitamin B12-lactoferrin complex), a method for the production thereof, and use thereof. A folic acid and/or vitamin $B_{12}$-lactoferrin complex of the present invention is characterized in that folic acid in the complex exhibits improved photostability, acid tolerance and solubility as compared to folic acid present by itself, and vitamin $B_{12}$ in the complex exhibits improved acid tolerance as compared to vitamin $B_{12}$ present by itself, and accordingly is useful as a material for foods, drinks and medicines.

2. Description of the Related Art

Folic acid which was discovered as an antianemic factor a long time ago is one of the vitamins essential for the body. Further, various enzymes are known to require folic acid as a coenzyme. Also, folic acid is extensively involved in the metabolisms of nucleotides, glycine, histidine, or the like, and the biosyntheses of proteins. Pteroylglutamate, 7,8-dihydropteroylglutamate, or the like and polyglutamin compounds thereof are also known as folic acid in a broad sense, and all of these compounds have physiological activities as folic acid. A deficiency in folic acid is known to cause abnormal myelopoietic functions (megaloblastic anemia), nervous disorder, intestinal dysfunction, or the like.

Recently, the higher probability of newborns having abnormal neural tubes due to a nutrient deficiency in mothers during pregnancy having particularly attracted attention in Europe and the United States, it has been revealed that this risk can be reduced by administering folic acid (Czeizel, A. E., J. Pediat. Gastroenterol. Nutr., vol. 20, pp. 4–16, 1995). Furthermore, it has been reported that an increase in homocysteine, which is associated with heart diseases, and a depletion of folic acid in the serum occur simultaneously (Jacob, R. A., M. M. Wu, S. M. Henning & M. E. Swendseid, J. Nutr., vol. 124, p. 1072, 1994). It has been also reported that folic acid exerts a preventive effect on cancer, particularly epithelial cancer (Glynn, S. A., D. Albanes, Nutr. Cancer, vol. 22, p. 101, 1994). Thus, the importance of folic acid is being recognized again.

On the other hand, folic acid is known to be relatively heat stable in the absence of oxygen. However, folic acid has low heat stability and storage stability in the presence of oxygen. For example, about 60% of folic acid was reported to be lost in cow's milk by heat sterilization or during storage (Renner E., Japanese Journal of Dairy & Food Science, vol. 35, p. A121–A135, 1996), and 25% of folic acid was lost in powdered milk (Oamen E. E., Hansen, A. P. M. & Swartzel, K. R., J. Dairy Sci., vol. 72, pp. 614–619, 1989). Furthermore, it is also known that folic acid is extremely sensitive to and rapidly decomposes in light and must be handled in the dark (Henderson B. G., Annu. Rev. Nutr., vol. 10, pp. 319–335, 1990).

The presence of a folic acid-binding protein in cow's milk is conventionally known (Ford, J. E., D. N. Salter & K. J. Scott, J. Dairy Res., vol. 36, p. 435, 1969). This folic acid-binding protein has a molecular weight of about 25 kDa, binds one molecule of folic acid, and is suggested to promote absorption from the intestinal tract (Said H. M., F. K. Ghishan & R. Redha, Am. J. Physiol., vol. 252, p. G229, 1987). However, the content of this folic acid-binding protein in milk is as low as 10 mg/L (Parodi P. W., Diet & Health News for New Zealand Health Professionals, vol. 27, pp. 1–4, 1998). Further, there has been no report on the photostability of this folic acid-binding protein.

As described above, folic acid has lately attracted considerable attention because of its important physiological functions, and the use of folic acid as a material for foods, drinks and medicines is desirable. However, there exists various limitations; for example, it is difficult to use folic acid, particularly in drinks, because of its poor photostability and solubility, which occasionally causes precipitation or requires shielding in packaging. Furthermore, as for the folic acid-binding protein, its content in milk is small and the outlook for its industrial scale production is still in doubt.

On the other hand, since vitamin $B_{12}$ is associated with the synthesis of heme, which is necessary for erythropoiesis, its deficiency is known to generate megaloblasts and cause anemia. Furthermore, since vitamin $B_{12}$ is essential for the generation and growth of cells, its deficiency causes inflammation of mucosal tissues, diarrhea, or the like. Vitamin $B_{12}$ is also known to have important roles in the reproductive functions and nervous system (Toru Fukui, "How to Take Vitamins and Minerals", Maruzen, 1997). Vitamin $B_{12}$ deficiency is attributed mainly to a vegetarian diet or often to gastrocectomy or abnormal absorption from the intestinal tract. Two extrasecretal proteins are known to be associated with vitamin $B_{12}$ absorption, i.e., haptocorrin secreted from the salivary gland (Toyoshima S., H. Saido, F. Watanabe, K. Miyatake and Y. Nakano, Abstract of XV International Congress of Nutrition, 204, 1993) and the intrinsic factor secreted from the stomach (Levine J. S., P. K. Nakane and R. H. Allen, Gastroenterology 79, 493, 1980); but the absorption mechanism is complicated. The recommended daily intake of vitamin $B_{12}$ for an adult in Japan is set to a low 2.4 µg. If this vitamin $B_{12}$ intake is obtained from food products, loss by cooking has to be taken into consideration. Furthermore, the recommended intake of vitamin $B_{12}$ per day for an adult in the United States, i.e., Optimal Daily Allowance (ODA), is set as 10 to 300 µg. A more positive intake of this vitamin will be required.

The presence of proteins which bind to vitamin $B_{12}$ in cow's milk has been suggested (Peter, W. P., Australian J. Dairy Tech., 53, 37–47, 1998). However, the whole picture of vitamin $B_{12}$ binding proteins has not yet been revealed. Vitamin $B_{12}$-binding bovine serum albumin (BSA) is the only one known protein (U.S. Pat. No. 4,082,738) and is being used in the quantification of erythrocytes (Japanese Patent Publication S57-5005281).

Further, vitamin $B_{12}$ is known to be relatively heat stable but not acid tolerant (Owen R. Fennema, Food Chemistry 3nd ed., Dekker, N.Y.). Accordingly, there is a need for a method to improve the stability, in particular the acid tolerance, of vitamin $B_{12}$ which has useful physiological functions.

Thus, both folic acid and vitamin $B_{12}$ are effective substances to ameliorate anemia or the like, but problems in stability restricts their use to limited areas.

SUMMARY OF THE INVENTION

In the present invention, it was newly found that lactoferrin interacts with folic acid and vitamin $B_{12}$ to form a folic acid and/or vitamin $B_{12}$-lactoferrin complex. Moreover, the folic acid in the complex has increased photostability and drastically increased solubility and is even stable in acid, as compared to folic acid present by itself, and vitamin $B_{12}$ in the complex has increased acid tolerance as compared to vitamin $B_{12}$ present by itself. Thus, the present invention has been completed. Accordingly, an object of the present invention is to provide a folic acid and/or vitamin $B_{12}$-lactoferrin complex in which folic acid and/or vitamin $B_{12}$ are incorporated into lactoferrin and a method for producing the same. Another object of the present invention is to provide medicines or foods and drinks prepared by using the folic acid and/or vitamin $B_{12}$-lactoferrin complex.

Lactoferrins to be used in the present invention can be those derived from milk, blood or the like. The source materials are not particularly restricted and can be derived from humans, bovines, hogs, or the like. Lactoferrins obtained by gene recombination can also be used. These lactoferrins can be those purified or partially purified, or materials having a low purity, such as WPC and skimmed milk powder. These lactoferrins can be used with or without heat treatment such as sterilization regardless of the state of bound iron. Further, lactoferrins carrying more than 2 iron molecules can be used (Japanese Patent Laid-open, No. H06-239900 and Japanese Patent Laid-open, No. H7-304798). It is also possible to use peptides which can be obtained by hydrolyzing lactoferrins with enzymes, such as pepsin and trypsin, or acid or alkaline. Further, in the present invention, lactoferrins also include transferrin and ovotransferrin. Lactoferrins used in the present invention thus imply the abovementioned lactoferrin-related substances.

DETAILED DESCRIPTION OF THE PREFERRED EMBODIMENT

First, a folic acid-lactoferrin complex will be explained as follows.

Folic acid to be used in the present invention is not particularly restricted and can be any products of a grade used for medical and pharmaceutical purposes to that used as a food additive.

A folic acid-lactoferrin complex can be prepared by mixing an aqueous folic acid solution and an aqueous lactoferrin solution, or by dissolving a powder of a mixture of folic acid and lactoferrin. Further, an aqueous solution in which sodium hydroxide, sodium bicarbonate, ammonium bicarbonate, sodium carbonate, and the like are mixed can be more effectively used since lactoferrins can incorporate a large amount of folic acid in an alkaline condition. The amount of folic acid being incorporated is maximally about 200 molecules per one molecule of lactoferrin.

TEST EXAMPLE 1

A lactoferrin solution at a concentration of 1 $\mu$mol/20 ml was prepared by dissolving lactoferrin in a 50 mM sodium bicarbonate aqueous solution (pH 8.5), and folic acid was added at a concentration of 10 to 300 $\mu$mol/20 ml. The resultant admixture was treated with an ultrafiltration (UF) membrane (cut-off molecular weight: 5 kDa; a product of Millipore Corp.) to separate it into the permeate and the retentate. Further, a 50 mM sodium bicarbonate aqueous solution (pH 8.5) was added to the remaining retentate to recover the permeate. This process was repeated four times and the resulting permeate was diluted 16 0,000-fold to recover the whole free folic acid into the permeate. The amount of binding-type folic acid remaining in the retentate was calculated from the amount of free folic acid contained in the recovered permeate obtained by measuring optical density at 362 nm.

Results are shown in Table 1.

Upon measuring the optical density for folic acid, it was confirmed that no protein was eluted into the permeate and no inhibiting substance derived from proteins existed. Further, a folic acid aqueous solution without protein was simultaneously subjected to the UF membrane treatment to prepare a control sample. These operations and measurements were performed in the dark to prevent decomposition of folic acid. No decomposition of folic acid during the measurement was confirmed by the optical density measurement.

TABLE 1

| Folic acid added ($\mu$mol) | Amount of folic acid held per 1 $\mu$mol of lactoferrin ($\mu$mol) |
|---|---|
| 10 | 9.3 |
| 50 | 40 |
| 100 | 79 |
| 200 | 160 |
| 300 | 210 |

The folic acid-lactoferrin complex can be concentrated by removing a low molecular weight fraction using UF membrane treatment, gel filtration, dialysis, or the like. Further, it can be easily made into a powder by an ordinary drying method. The obtained powder had excellent solubility.

TEST EXAMPLE 2

A light radiation test was carried out with a folic acid-lactoferrin complex. Namely, to a 1 $\mu$mol lactoferrin solution which was prepared by dissolving lactoferrin into 50 ml of a 50 mM sodium bicarbonate aqueous solution (pH 8.5) was added folic acid to make a 100 $\mu$mol solution. The resultant admixture was subjected to dialysis using a dialysis membrane (cut-off molecular weight: 10 kDa) against a 5 mM phosphate buffer solution (pH 6.5) and then to freeze-drying to obtain a folic acid-lactoferrin complex. The resulting folic acid-lactoferrin complex powder was dissolved in a 50 mM phosphoric acid buffer solution (pH 6.5) at a concentration of 3 mg/100 ml. Separately, folic acid (a product of Sigma) was dissolved in a 50 mM phosphoric acid buffer solution (pH 6.5) at a concentration of 0.8 mg/100 ml. Each sample solution (5 ml) was dispensed into a transparent polyethylene container, water was added to a depth of 5 mm, and the solution was subjected to radiation with a 40-watt fluorescent lump from a height of 30 mm, after which the amount of folic acid was measured by a method using microorganisms. Namely, the pH of the folic acid-lactoferrin complex sample was adjusted to 2.0, 2 mg of pepsin (a product of Sigma) per 1 ml sample were added, and proteolysis was carried out at 37 C for 120 minutes, after which the pH was further adjusted to 7.5, 2 mg of trypsin (a product of Sigma) per 1 ml sample were added, and proteolysis was carried out at 37 C for 120 minutes. After deaeration, the reaction solution was heated for 5 minutes and centrifuged at 15,000 G to recover the supernatant. The amount of folic acid was measured by a method using microorganisms (Davis, R. E., D. J. Nicol & A. Kelly, J. Clin. Path., vol. 23, pp. 47–53, 1970). Further, a calibration curve was obtained by using folic acid (a product of Sigma). These operations and measurements were carried out in the dark except for the fluorescent radiation.

Results are shown in Table 2

TABLE 2

| Radiation time (min) | Folic acid ($\mu$mol/10 ml) | |
| --- | --- | --- |
| | Folic acid-lactoferrin complex | Folic acid |
| 0 | 0.17 | 0.16 |
| 0.5 | 0.16 | 0.13 |
| 7 | 0.14 | 0.03 |
| 24 | 0.11 | — |

A comparison of the folic acid aqueous solution and the folic acid-lactoferrin complex aqueous solution, in which the same molarity of folic acid was dissolved, revealed that deterioration by light was markedly delayed in the folic acid-lactoferrin complex.

TEST EXAMPLE 3

Folic acid and the folic acid-lactoferrin complex used in Test Example 2 were each added to deionized water at a folic acid concentration of 0.1 to 10 $\mu$mol/10 ml to measure turbidity at 660 nm.

Results are shown in Table 3

TABLE 3

| Folic acid concentration ($\mu$mol/10 ml) | Folic acid-lactoferrin complex | Folic acid |
| --- | --- | --- |
| 0.1 | 0.002 (Transparent, yellow) | 0.01 (Slightly turbid) |
| 1.0 | 0.002 (Transparent, yellow) | 0.025 (Insoluble) |
| 10 | 0.003 (Transparent, yellow) | 0.034 (Insoluble) |

The solubility of folic acid in deionized water was more than 10 $\mu$mol/10 ml in the folic acid-lactoferrin complex aqueous solution while it was less than 0.1 $\mu$mol/10 ml in a folic acid aqueous solution.

It was thus evident that folic acid had a markedly improved photostability and excellent solubility in the folic acid-lactoferrin complex.

TEST EXAMPLE 4

Folic acid and the folic acid-lactoferrin complex used in Test Example 2 were each added to a 10 mM citric acid buffer solution (pH 2.5) at a folic acid concentration of 0.25 $\mu$mol/10 ml. Next, 50 ml portions of the solutions were dispensed in brown bottles, sterilized at 90 C for 30 minutes and then stored at 37 C. The amount of folic acid was measured in the same manner as in Test Example 2.

TABLE 4

| | Folic acid ($\mu$mol/10 ml) | |
| --- | --- | --- |
| | Folic acid-lactoferrin complex | Folic acid |
| Before heat pasteurization | 0.28 | 0.28 |
| Immediately after heat pasteurization | 0.26 | 0.18 |
| Stored for 2 months | 0.22 | 0.05 |
| Stored for 4 months | 0.20 | 0.01 |

The results above revealed that the stability of folic acid under acidic conditions was better in the folic acid-lactoferrin complex.

Next, a vitamin $B_{12}$-lactoferrin complex will be explained as follows.

Vitamin $B_{12}$ to be used in the present invention is not particularly restricted and can be any products of a grade used for medical and pharmaceutical purposes to that used a food additive.

A folic acid-lactoferrin complex can be prepared by mixing an aqueous vitamin $B_{12}$ solution and an aqueous lactoferrin solution, or by dissolving a powder of a mixture of vitamin $B_{12}$ and lactoferrin. The amount of vitamin $B_{12}$ being carried is maximally about 100 molecules per one molecule of lactoferrin.

TEST EXAMPLE 5

A lactoferrin solution at a concentration of 0.1 $\mu$mol/20 ml was prepared by dissolving lactoferrin in a 50 mM imidazole buffer solution (pH 6.5), and vitamin $B_{12}$ was added at a concentration of 1 to 50 $\mu$mol/20 ml. The resultant solution was treated with a UF membrane (cut-off molecular weight: 5 kDa; a product of Millipore Corp.) to separate it into the permeate and the retentate. Further, a 50 mM imidazole buffer solution (pH 6.5) was added to the remaining retentate to recover the permeate. This process was repeated four times and the resulting permeate was diluted 16 0,000-fold to recover whole free vitamin $B_{12}$ into the permeate. Further, the pH of the vitamin $B_{12}$-lactoferrin complex sample in the retentate was adjusted to 2.0, 2 mg of pepsin (a product of Sigma) per 1 ml sample were added, and proteolysis was carried out at 37 C for 60 minutes, after which the pH was further adjusted to 7.5, 2 mg of trypsin (a product of Sigma) per 1 ml sample were added, and proteolysis was carried out at 37 C for 120 minutes. After heating, the supernatant was recovered by centrifugation at 15,000 G. The amount of vitamin $B_{12}$ was measured by a method using microorganisms (Encyclopedia of Vitamins, the Japanese Association of Vitaminology, Asakura Shoten, p. 501, 1996). Further, a calibration curve was obtained by using cyanocobalmin (a product of Sigma).

Results are shown in Table 5.

TABLE 5

| Vitamin $B_{12}$ added ($\mu$mol) | Amount of vitamin $B_{12}$ held per 1 $\mu$mol of lactoferrin ($\mu$mol) |
| --- | --- |
| 10 | 4.2 |
| 100 | 41 |
| 500 | 130 |

The vitamin $B_{12}$-lactoferrin complex can be concentrated by removing a low molecular weight fraction using UF membrane treatment, gel filtration, dialysis, or the like. Further, it can be easily made into a powder by an ordinary drying method. The obtained powder had excellent solubility.

TEST EXAMPLE 6

To a 0.1 $\mu$mol lactoferrin solution which was prepared by dissolving lactoferrin into 50 ml of a 50 mM imidazole buffer solution (pH 6.5) was added vitamin $B_{12}$ to make a 20 $\mu$mol solution. The resultant admixture was subjected to dialysis using a dialysis membrane (cut-off molecular weight: 5 kDa) against deionized water and then to freeze-drying to obtain a vitamin $B_{12}$-lactoferrin complex in which 57 molecules of vitamin $B_{12}$ were held per one molecule of lactoferrin. The resulting vitamin $B_{12}$-lactoferrin complex was dissolved in a 50 mM imidazole buffer solution (pH 6.5)

or a 50 mM citric acid buffer solution (pH 3.0) at a concentration of 14 μg/100 ml. Separately, as a control, vitamin $B_{12}$ (a product of Sigma) was dissolved in a 50 mM imidazole buffer solution (pH 6.5) or a 50 mM citric acid buffer solution (pH 3.0) at a concentration of 5.6 μg/100 ml. Portions (5 ml) of each sample solution were dispensed into heat-resistant glass bottles and sealed, sterilized at 90 C for 30 minutes and then stored at 35 C for 2 months. The reduction rates of vitamin $B_{12}$ were measured. The amount of vitamin $B_{12}$ was measured in the same manner as in Test Example 5.

TABLE 6

|  | Vitamin $B_{12}$ reduction rate (%) | |
|---|---|---|
|  | pH 7.5 | pH 3.0 |
| Vitamin $B_{12}$-lactoferrin complex | 12% | 16% |
| Vitamin $B_{12}$ | 8% | 48% |

The results above revealed that the acid tolerance of vitamin $B_{12}$ in the vitamin $B_{12}$-lactoferrin complex was markedly improved.

[Description of the Embodiments of the Invention]

In the present invention, a folic acid and/or vitamin $B_{12}$-lactoferrin complex in which lactoferrin carries folic acid and/or vitamin $B_{12}$ is produced by mixing a folic acid and/or vitamin $B_{12}$ and lactoferrin. This folic acid and/or vitamin $B_{12}$-lactoferrin complex can be used for the purpose of nutritional enhancement in medicines, foods, drinks, animal feeds, or the like. Further, because of its high photostability, it can be used as a solution, powder, paste, tablet, or the like without any particular restriction.

The present invention will be explained more in detail referring to the following Examples.

EXAMPLE 1

A mixture of 6 mmol of folic acid (a product of Japan Roche K.K.) and 1.2 mmol of lactoferrin (a product of TATUA) was dissolved in 100 L of deionized water. The resulting solution was reacted at 10 C overnight, and then concentrated by treating with a UF membrane (cut-off molecular weight: 50 kDa). The resulting solution (2 L) was freeze-dried to obtain 81 g of a folic acid-lactoferrin complex powder. The amount of folic acid in this powder was measured by the method of Test Example 2, which revealed that 2 molecules of folic acid were held per one molecule of lactoferrin.

EXAMPLE 2

Folic acid (870 mmol, a product of Japan Roche K.K.) was dissolved in 100 L of a 2% sodium bicarbonate aqueous solution, and 2 mmol of lactoferrin (a product of TATUA) were further mixed, after which the admixture was concentrated and desalted by treating with a UF membrane (cut-off molecular weight: 50 kDa). The resulting solution (2 L) was spray-dried, using a test-oriented spray-dryer, to obtain 240 g of a folic acid-lactoferrin complex powder. The amount of folic acid in this powder was measured by the method of Test Example 2, which revealed that 210 molecules of folic acid were held per one molecule of lactoferrin.

EXAMPLE 3

Folic acid (110 mmol, a product of Japan Roche K.K.) was dissolved in 80 L of tap water while adjusting the pH to 9 with a 1N sodium hydroxide aqueous solution, and 0.6 mmol of lactoferrin (a product of TATUA) was further mixed. The admixture was allowed to stand for 1 hour and then concentrated and desalted by treating with a UF membrane (cut-off molecular weight: 50 kDa). The resulting solution (2 L) was frozen at −40 C to store as a frozen liquid concentrate of folic acid-lactoferrin complex. The amount of folic acid in this frozen liquid concentrate was measured by the method of Test Example 2, which revealed that 82 molecules of folic acid were held per one molecule of lactoferrin. Further, no precipitate or the like was observed when the frozen liquid concentrate was defrosted at room temperature.

EXAMPLE 4

A solution (1 L) containing 1.2 mol of sodium bicarbonate, 10 μmol of lactoferrin (a product of DMV) and 0.5 mmol of folic acid (solution A) and 1L of solution containing 1.5 mmol (as iron ions) of ferric sulfate were prepared. A lactoferrin complex having iron and folic acid were prepared by adding solution A to solution B, and concentrated and desalted by treating with a UF membrane (cut-off molecular weight: 5 kDa). The amount of folic acid in this complex was measured by the method of Test Example 2, which revealed that 27 molecules of folic acid were held per one molecule of lactoferrin. The amount of iron was measured by atomic absorption spectrometry, which revealed that 148 molecules of iron were held per one molecule of lactoferrin.

EXAMPLE 5

Vitamin $B_{12}$ (300 g, a product of Japan Roche K.K.) was dissolved in 300 L of deionized water, and 100 g of lactoferrin (a product of TATUA) were further mixed. The admixture was reacted at 20 C for 8 hours and then fractionated by treating with a UF membrane (cut-off molecular weight: 50 kDa) to remove free vitamin $B_{12}$ and further concentrated. The resulting solution (1 L) was spray-dried, using a test-oriented spray-dryer, to obtain 220 g of a vitamin $B_{12}$-lactoferrin complex powder. The amount of vitamin $B_{12}$ in this powder was measured by the method of Test Example 5, which revealed that 83 molecules of vitamin $B_{12}$ were held per one molecule of lactoferrin. Further, the solubility of this powder was good.

EXAMPLE 6

A solution (1 L) containing 0.05 mol of calcium carbonate and 1.2 mol of ammonium bicarbonate having a pH 7.8 adjusted with hydrochloric acid (solution A), a solution (0.2 L) containing 1.5 mol (as iron ions) of ferric sulfate (solution B1), and a solution (0.8 L) containing 10 μmol of transferrin (apo-type, highly purified, derived from bovine plasma; a product of Wako Pure Chemical Industries, Ltd.) and 1 mmol of vitamin $B_{12}$ (solution B2) were prepared. A transferrin complex having iron and vitamin $B_{12}$ was prepared by mixing solution B1 and solution B2 and adding solution A to the mixture, and then concentrated and desalted by treating with a UF membrane (cut-off molecular weight: 5 kDa) to prepare 100 ml of liquid concentrate of the complex. The amount of vitamin $B_{12}$ in this complex was measured by the method of Test Example 5, which revealed that 32 molecules of vitamin $B_{12}$ were held per one molecule of lactoferrin. The amount of iron was measured by atomic absorption spectrometry, which revealed that 139 molecules of iron were held per one molecule of lactoferrin.

EXAMPLE 7

Folic acid (50 mmol) was dissolved in 10 L of a 2% sodium bicarbonate aqueous solution. Separately, 0. 38 mmol of lactoferrin (a product of DMV) and 20 mmol of vitamin $B_{12}$ (a product of Japan Roche K.K.) were dissolved in 30 L of deionized water. Next, these solutions were mixed and the mixture was stirred at room temperature for 2 hours, and then concentrated and desalted by treating with a UF membrane (cut-off molecular weight: 5 kDa) to prepare a folic acid and vitamin $B_{12}$-lactoferrin complex. The complex was freeze-dried into a powder. The amounts of folic acid and vitamin $B_{12}$ in this powder were measured by the method of Test Example 2 and Test Example 5, which revealed that 79 molecules of folic acid and 24 molecules of vitamin $B_{12}$ were held per one molecule of lactoferrin.

EXAMPLE 8

A solution (1 L) containing 1.0 mol of sodium bicarbonate and 2 mmol of folic acid (a product of Japan Roche K.K.) (solution A), a solution (0.2 L) containing 1 mmol (as iron ions) of ferric chloride (solution B1), and a solution (0.8 L) containing 10 μmol of bovine lactoferrin (a product of ULN) and 400 μmol of vitamin $B_{12}$ (a product of Japan Roche K.K.) (solution B2) were prepared. Solution B 1 and solution B2 were mixed, then solution A was added, and sodium bicarbonate was appropriately added to maintain the pH of the solution at 8.5 to prepare a folic acid and vitamin $B_{12}$-lactoferrin complex, which was then concentrated and desalted by treating with a UF membrane (cut-off molecular weight: 5 kDa) and freeze-dried into a powder. The amounts of folic acid, vitamin $B_{12}$ and iron in this powder were measured by the method of Test Example 2, Test Example 5, and atomic absorption spectrometry, which revealed that 90 molecules of folic acid, 4 molecules of vitamin $B_{12}$, and 96 molecules of iron were held per one molecule of lactoferrin.

EXAMPLE 9

Lactoferrin (20 g) was dissolved in 100 g of deionized water and the pH of the solution was adjusted to 2.0 with hydrochloric acid. To this solution, 100 mg of pepsin (a product of Sigma) was added, and the reaction was carried out at 37 C for 2 hours to prepare a lactoferrin hydrolysate. After the reaction, the pH was adjusted to 7.0 and the reaction solution was freeze-dried. Folic acid (20 mmol) was dissolved in 100 L of 10% sodium carbonated aqueous solution. Separately, 10 g of the lactoferrin hydrolysate prepared as above and 15 mmol of vitamin $B_{12}$ (a product of Japan Roche K.K.) were dissolved in 30 L of deionized water. Next, these solutions were then mixed and the mixture was stirred at room temperature for 2 hours, and then concentrated and desalted by treating with a UF membrane (cut-off molecular weight: 5 kDa) to prepare a folic acid and vitamin $B_{12}$-lactoferrin complex. The complex was freeze-dried to obtain 23 g of folic acid and vitamin $B_{12}$-lactoferin complex powder. The amounts of folic acid and vitamin $B_{12}$ in this powder were measured by the method of Test Example 2 and Test Example 5, which revealed that 130 molecules of folic acid and 53 molecules of vitamin $B_{12}$ were held per one molecule of lactoferrin.

EXAMPLE 10

A health drink was produced by using the folic acid-lactoferrin complex prepared in Example 2. Namely, 48 g of the folic acid-lactoferrin complex were dissolved in 10 kg of ion exchange water, 2,200 kg of ion exchange water were further added and stirred, and 300 kg of trehalose (a product of Hayashibara Co., Ltd.) and 1.2 kg of stevia (a product of Maruzen Seiyaku K.K.) were further added, stirred and dissolved. Next, 15 kg of citric acid (a product of Wako Pure Chemical, Co., Ltd.) were added and stirred, 6 kg of flavor were added, and deionized water was added to adjust the total weight to 3,000 kg. The admixture was sterilized by heating (85 C, 15 seconds) using a plate-type heat sterilizer and dispensed into transparent bottles, further kept in hot water at 85 C for 15 minutes, and then cooled to produce a health drink. This health drink was subjected to a radiation test under a fluorescent light under refrigeration for about one month, which revealed that the color did not change and no precipitation or the like occurred.

As a control, a health drink was produced in the same manner except that 2.0 g of folic acid (a product of Japan Roche K.K.) were added in place of the complex. This health drink was slightly turbid immediately after production. A radiation test under a fluorescent light under refrigeration for about one month revealed that color turned yellow and precipitation occurred.

Analyses showed a 64% decrease in the amount of folic acid in the health drink with folic acid, while the decrease was 8% in the health drink with the folic acid-lactoferrin complex.

EXAMPLE 11

Chewable tablets were produced according to an ordinary method by mixing 160 mg of the folic acid-lactoferrin complex prepared in Example 2, 64.3 kg of maltitol, 25.5 kg of palatinit, 0.2 kg of aspertame, 3.0 kg of citric acid, 3.0 kg of emulsifier, and 4.0 kg of flavor.

The resulting chewable tablets had no particular problem with flavor or the like. Further, the tablets were stored in a transparent plastic container under a fluorescent light at 50 C for 4 weeks. The amount of folic acid measured after storage was almost the same as that measured immediately after production.

EXAMPLE 12

A health drink was produced by using the vitamin $B_{12}$-lactoferrin complex prepared in Example 5. Namely, 900 mg of the vitamin $B_{12}$-lactoferrin complex were dissolved in 10 kg of ion exchange water, 2,200 kg of ion exchange water were further added and stirred, and 300 kg of trehalose (a product of Hayashibara Co., Ltd.) and 1.2 kg of stevia (a product of Maruzen Seiyaku K.K.) were further added, stirred and dissolved. Next, 15 kg of citric acid (a product of Wako Pure Chemical, Co., Ltd.) were added and stirred, 6 kg of flavor were added, and deionized water was added to adjust the total weight to 3,000 kg. The admixture was sterilized by heating (85 C, 15 seconds) using a plate-type heat sterilizer and dispensed into transparent bottles, further kept in hot water at 85 C for 15 minutes, and then cooled to produce a health drink. As a control, a health drink was produced in the same manner except that 630 mg of vitamin $B_{12}$ (a product of Japan Roche K.K.) were added in place of the complex. These health drinks were stored at 37 C for 4 months, and then the amount of vitamin $B_{12}$ was measured. Measurement revealed a 58% decease in the amount of vitamin $B_{12}$ in the health drink with vitamin $B_{12}$, while the decrease was 11% in the health drink with the vitamin $B_{12}$-lactoferrin complex.

EXAMPLE 13

The folic acid and vitamin $B_{12}$-lactoferrin complex prepared in Example 7 (1.8 kg) was dissolved in 10 kg of water, and 200 kg of water, then 5.8 kg of stabilizer (a product of Taiyoh Kagaku Co., Ltd.) were further added. Further, 780 kg of water, then 140 kg of sugar, 100 kg of Japanese apricot flesh, 1.6 kg of citric acid, 0.4 kg of trisodium citrate, and 0.18 kg of flavoring (a product of Hasegawa Koryo K.K.) were added, dissolved and then dispensed into retort pouches. They were subjected to retort pasteurization by heating at 120 C for 12 minutes to produce a jelly product. As a control, a jelly product was produced in the same way except that 410 μg/L of folic acid and 320 μg/L of vitamin $B_{12}$ were added in place of the complex. These products were stored at 20 C for 3 months, and then the amounts of folic acid and vitamin $B_{12}$ were measured. Measurement revealed a 28% decrease for folic acid and a 35% decrease for vitamin $B_2$ in the jelly with folic acid and vitamin $B_2$ present by themselves, while the decreases were 6% for folic acid and 7% for vitamin $B_{12}$ in the jelly with folic acid and vitamin $B_{12}$-lactoferrin complex.

EXAMPLE 14

The folic acid and vitamin $B_{12}$-lactoferrin complex prepared in Example 8 (10 g) was dissolved in 10 kg of water, and 200 kg of water, then 5.8 kg of stabilizer (a product of Taiyoh Kagaku Co., Ltd.) were further added. Further, 780 kg of water, then 140 kg of sugar, 100 kg of Japanese apricot flesh, 1.6 kg of citric acid, 0.4 kg of trisodium citrate, and 0.18 kg of flavoring (a product of Hasegawa Koryo K.K.) were added, dissolved and then dispensed into retort pouches. They were subjected to retort pasteurization by heating at 120 C for 12 minutes to produce a jelly product. As a control, a jelly product was produced in the same way except that 310 μg/100 ml of folic acid and 25 μg/100 ml of vitamin $B_{12}$ were added in place of the complex. These products were stored at 20 C for 3 months, and then the amounts of folic acid and vitamin $B_{12}$ were measured. Measurements revealed a 24% decrease for folic acid and a 30% decrease for vitamin $B_{12}$ in the jelly with folic acid and vitamin $B_{12}$ present by themselves, while the decreases were 5% for folic acid and 7% for vitamin $B_{12}$ in the jelly with folic acid and vitamin $B_{12}$-lactoferrin complex.

[Effectiveness of the Invention]

A folic acid and/or vitamin $B_{12}$-lactoferrin complex is useful as a material for foods, drinks and medicines because folic acid in the complex characteristically has increased photostability, heat tolerance and solubility as compared to folic acid present by itself, and vitamin $B_{12}$ in the complex characteristically has increased acid tolerance as compared to vitamin $B_{12}$ present by itself.

What is claimed is:

1. A folic acid and/or vitamin $B_{12}$-lactoferrin complex, characterized in that the lactoferrin holds folic acid and/or vitamin $B_{12}$.

2. A method for producing a folic acid and/or vitamin $B_{12}$-lactoferrin complex as claimed in claim 1, comprising mixing folic acid and/or vitamin $B_{12}$ with lactoferrin.

3. Foods, drinks or medicines prepared by adding the folic acid and/or vitamin $B_{12}$-lactoferrin complex as claimed in claim 1.

4. A composition containing at least one of folic acid or vitamin $B_{12}$, said folic acid or vitamin $B_{12}$ being bound to lactoferrin and forming a complex.

5. A composition as claimed in claim 4, which contains substantially no free form of folic acid or vitamin $B_{12}$.

6. A composition as claimed in claim 4, which is desalted.

7. A composition as claimed in claim 4, wherein two to 210 molecules of folic acid per molecule of lactoferrin are bound in the complex.

8. A composition as claimed in claim 4, wherein two to 150 molecules of vitamin $B_{12}$ per molecules of lactoferrin are bound in the complex.

9. A composition as claimed in claim 4, further comprising iron which is bound to lactoferrin in the complex.

10. A composition as claimed in claim 4, wherein at least 20 molecules of folic acid or vitamin $B_{12}$ per molecule of lactoferrin are bound in the complex.

11. A folic acid/vitamin $B_{12}$-enriched food or drink comprising a composition as claimed in claim 4.

12. A folic acid/vitamin $B_{12}$-enriched food or drink as claimed in claim 11, wherein the composition contains substantially no free form of folic acid or vitamin $B_{12}$.

13. A folic acid/vitamin $B_{12}$-enriched food or drink as claimed in claim 11, wherein the composition is desalted.

14. A folic acid/vitamin $B_{12}$-enriched food or drink as claimed in claim 11, further comprising iron bound to lactoferrin.

15. A method for producing a folic acid and/or vitamin $B_{12}$-lactoferrin complex, comprising mixing folic acid and/or or vitamin $B_{12}$ with lactoferrin in a solution at a pH of 8.0 or higher.

* * * * *